United States Patent
Queiroz

(10) Patent No.: US 9,572,770 B2
(45) Date of Patent: Feb. 21, 2017

(54) STABLE TOPICAL COMPOSITION AND A PROCESS FOR PRODUCING A STABLE TOPICAL COMPOSITION

(75) Inventor: Dinalva Brito de Queiroz, Eusébio (BR)

(73) Assignee: EVIDENCE SOLUCÕES FARMACÊUTICAS LTDA EPP, Fortaleza, CE (BR)

( * ) Notice: Subject to any disclaimer, the term of this patent is extended or adjusted under 35 U.S.C. 154(b) by 342 days.

(21) Appl. No.: 13/811,516

(22) PCT Filed: Jul. 21, 2011

(86) PCT No.: PCT/BR2011/000241
§ 371 (c)(1),
(2), (4) Date: Jan. 22, 2013

(87) PCT Pub. No.: WO2012/009778
PCT Pub. Date: Jan. 26, 2012

(65) Prior Publication Data
US 2013/0123220 A1    May 16, 2013

(30) Foreign Application Priority Data
Jul. 22, 2010   (BR) ..................................... 1002486

(51) Int. Cl.
| A61K 31/56 | (2006.01) |
| A61K 9/00 | (2006.01) |
| A61K 8/06 | (2006.01) |
| A61K 8/36 | (2006.01) |
| A61K 8/37 | (2006.01) |
| A61K 8/39 | (2006.01) |
| A61K 8/49 | (2006.01) |
| A61K 8/55 | (2006.01) |
| A61K 8/63 | (2006.01) |
| A61K 9/107 | (2006.01) |
| A61K 31/565 | (2006.01) |
| A61K 31/568 | (2006.01) |
| A61K 31/57 | (2006.01) |
| A61K 47/12 | (2006.01) |
| A61K 47/24 | (2006.01) |
| A61K 47/26 | (2006.01) |
| A61K 47/44 | (2006.01) |
| A61Q 19/00 | (2006.01) |

(52) U.S. Cl.
CPC ............ *A61K 9/0014* (2013.01); *A61K 8/06* (2013.01); *A61K 8/361* (2013.01); *A61K 8/37* (2013.01); *A61K 8/39* (2013.01); *A61K 8/4973* (2013.01); *A61K 8/553* (2013.01); *A61K 8/63* (2013.01); *A61K 9/1075* (2013.01); *A61K 31/565* (2013.01); *A61K 31/568* (2013.01); *A61K 31/57* (2013.01); *A61K 47/12* (2013.01); *A61K 47/24* (2013.01); *A61K 47/26* (2013.01); *A61K 47/44* (2013.01); *A61Q 19/00* (2013.01); *A61K 2800/21* (2013.01); *A61K 2800/805* (2013.01)

(58) Field of Classification Search
CPC ... A61K 8/06; A61K 8/37; A61K 8/39; A61K 8/4973; A61K 8/553; A61K 8/63; A61K 8/361; A61K 9/0014; A61K 9/1075; A61K 31/565; A61K 31/568; A61K 31/57; A61K 47/12; A61K 47/24; A61K 47/26; A61K 47/44; A61K 2800/21; A61K 2800/805; A61Q 19/00
USPC ........................................................ 514/170
See application file for complete search history.

(56) References Cited

U.S. PATENT DOCUMENTS

| 6,117,915 A * | 9/2000 | Pereira .................... A61K 8/062 424/59 |
| 7,105,184 B2 * | 9/2006 | Pauly et al. ................... 424/725 |
| 2002/0106390 A1 | 8/2002 | Huglin et al. |
| 2002/0155084 A1 * | 10/2002 | Roessler .............. A61K 9/1075 424/70.21 |
| 2002/0159952 A1 * | 10/2002 | Unger .......................... 424/9.51 |
| 2004/0115159 A1 | 6/2004 | Tadlock et al. |
| 2007/0065390 A1 * | 3/2007 | Spengler ................. A61K 8/068 424/70.21 |
| 2007/0085058 A1 | 4/2007 | Mora-Gutierrez et al. |
| 2007/0264349 A1 | 11/2007 | Lee et al. |
| 2009/0324727 A1 | 12/2009 | Foguet Roca |
| 2011/0008305 A1 | 1/2011 | Yu et al. |

(Continued)

FOREIGN PATENT DOCUMENTS

| WO | WO 2006/087156 | 8/2006 |
| WO | WO 2009093104 A2 * | 7/2009 ............. A61K 8/922 |

OTHER PUBLICATIONS

Chang et al. (Inhibition of platelet activation and endothelial cell injury by polyphenolic compounds isolated from Lonicera japonica Thunb, Prostaglandins, Leukotrienes and Essential Fatty Acids (PLEFA), (Apr. 1992) 45(4): 307-312 (Abs. only), ([Retrieved from internet <URL: http://www.sciencedirect.com/science/article/pii/ 095232789290088Z >] [Downloaded Jan. 16, 2015], 3 pages).*

(Continued)

*Primary Examiner* — Anna Pagonakis
*Assistant Examiner* — Miriam A Levin
(74) *Attorney, Agent, or Firm* — B. Aaron Schulman, Esq.; Stites & Harbison, PLLC.

(57) ABSTRACT

The present invention is directed to a suitable topical composition for cosmetic, pharmaceutical or dermatological use. In a particular aspect, it is a stable nanoemulsion whose particles have a narrow size distribution range. In another particular aspect, the invention is directed to an improved process for producing said composition.

8 Claims, No Drawings

(56) References Cited

U.S. PATENT DOCUMENTS

2011/0021439 A1* 1/2011 Amari .................. A61K 8/922
                                                    514/18.8
2011/0045050 A1* 2/2011 Elbayoumi .......... A61K 9/1075
                                                    424/423
2011/0159105 A1* 6/2011 Vilinsky ...................... 424/600

OTHER PUBLICATIONS

International Search Report for PCT/BR2011/000241 dated Dec. 19, 2012.
Written Opinion of the International Searching Authority for PCT/BR2011/000241 dated Dec. 19, 2012.
Database WPI, Week 200961, Thomson Scientific, London, GB; AN 2009-M83514, XP002688659, & KR 2009 0085246 A (Hanbul Cosmetics Co Ltd) (Aug. 7, 2009) Abstract.
Torchilin-Ed, Wladimir P., Nanoparticles as Drug Carriers, Imperial College Press, 2006.
Gonzaga, et al, "Nanotechnology in Hormone Replacement Therapy: Safe and Efficacy of Transdermal Estriol and Estradiol Nanoparticles after 5 Years Follow-Up Study", 2012, pp. 442-450, vol. 31, No. 3, Lat. Am. J. Pharm.

* cited by examiner

STABLE TOPICAL COMPOSITION AND A PROCESS FOR PRODUCING A STABLE TOPICAL COMPOSITION

DISCLOSURE OF THE INVENTION

The present invention is directed to a stable topical composition that is suitable for cosmetic, pharmaceutical or dermatological uses. In a particular aspect, it is directed to a stable nanoemulsion the particles of which have advantageously a narrow size distribution range. In another particular aspect, the present invention is directed to an improved process for producing said composition.

BACKGROUND OF THE INVENTION

Topical products are being developed continuously nowadays, either to have an effect on the skin or to dispense products through the skin.

Nanoemulsions are colloidal systems that also include micelles, liposomes, virosomes, nano suspensions, micro emulsions and polymeric solutions. Nanoemulsions, based on their physical and chemical characteristics, are a subgroup of micro emulsions.

Micro emulsions are aqueous dispersions of particles composed of a lipid nucleus surrounded by monolayers of surfactants and co-surfactants.

Usually, microemulsions are produced through the mechanical fragmentation of an oleous phase in an aqueous phase in the presence of a surfactant. As is known, the very small size of oleous globules is attained by at least one passage through a high-pressure homogenizer or sonicator. It is generally known that the small size of the globules and the high homogeneity thereof distinguish microemulsions from conventional emulsions, as they are able to carry active agents more efficiently, endowing them with an increasing importance in cosmetic, medicine, and dermatology.

The present invention aims at improving a nanoemulsion-based composition. As understood herein, the composition is nanostructured by virtue of the fact that nanoscale particles are present therein.

DESCRIPTION OF THE INVENTION

In a first aspect, the present invention concerns a stable topical composition that comprises a specific oil-in-water nanoemulsion produced through a simple process that does not require a high-pressure homogenizer or a sonicator, wherein the oleous phase dispersed in the aqueous phase has a narrow particle size distribution, and can be modulated to efficiently dispense one or more active principles incorporated in its nanoparticles, both dermally and transdermally.

Some advantages of the composition of the invention, in relation to the actives it aims at dispensing dermally or transdermally, in the medicamentous area, are:
Excellent absorption through the skin;
High bioavailability;
Less administrations per day;
Absence of first pass metabolism (in the liver)
No unpleasant flavor (by avoiding oral administration);
Easy adaptation to change of dose;
Easy application and consequent higher adhesion of the patient to the therapy.

Thus, the invention is about a stable topical composition characterized by being composed of at least (a) a nanoemulsion that comprises at least one non-ionic emulsifying agent, at least one amphoteric surfactant, at least one emollient, at least one humectant, and at least a hydrating agent, and (b) one or more active principles incorporated to the nanoemulsion oleous globules, optionally in the presence of one or more amongst oxygen-carrying agents, oleous vehicles, permeation promoters and hydrating agents.

Without excluding any other, non-ionic emulsifying agents suitable for the invention are one or more amongst cetearyl, sorbitan and ceteareth (particularly ceteareth having an ethoxylation between 6 and 20) of mixtures of fatty acid salts resulting from the saponification of vegetable oil, for example, coconut oil (cocoate), palm oil (palmate), olive oil (olivate), soy oil (soyate), sunflower seed oil, or animal oil (tallowate). Particularly one or more amongst cetearyl olivate, sorbitan olivate and ceteareth-6 olivate are used.

Without excluding any other, amphoteric surfactants suitable for the invention are one or more amongst natural ones such as saponines, lecithin and soy protein. Particularly, lecithin is used.

Without excluding any other, emollients suitable for the invention are one or more fatty acids among (a) those having a carbon chain between $C_{10}$ and $C_{18}$, (b) long chain polyunsaturated ones such as arachidonic, eicosapentaenoic, docosahexanoic acid, as well as acids of the omega 3, omega 6 and omega 9 family, and (c) triglycerides of palmitic, oleic, linoleic, capric and caprylic acid. Particularly, use is made of a mixture of linolenic (omega 3) acid, linoleic (omega 6) acid and oleic (omega 9) acid.

Without excluding any other, humectants suitable for the invention are one or more amongst polypropylene glycol, glycerin, panthenol, hyaluronic acid and chondroitin sulfate. Particularly, propylene glycol is used.

Without excluding any other, hydrating agents that are suitable for the invention are one or more amongst disaccharides such as trehalose, maltose, and sucrose. Particularly, trehalose is used.

Without excluding any other, adequate oxygen-carrying agents are perfluorocarbon compounds, for example, perfluorotrialkylamine (preferably alkyl having 1 to 3 carbons), perfluorohexane, perfluorodimethylciclohexane, octofluorooctane and perfluorodecalin. Particularly, perfluorodecalin or a mixture of perfluorodecalin and perfluorotripropylamine is used. Within a particular embodiment of the invention, wherein an oxygen-carrying agent is used, it is contained in a liposome, for example of phosphatidylcholine.

There is no specific restriction as to the active principles contained in the composition of the invention that may be dermally or transdermally dispensed, by way of topical application. Particularly, without excluding any other, adequate active principles are the ones orally administered in situations where one or more of the following problems are present: the patient has difficulty in swallowing, unpleasant flavor, low bioavailability, low solubility, large chemical structures degraded into undesirable metabolites, sensitivity to acidity or variation of acidity in the gastrointestinal tract, reduced concentration of the active principle through systemic metabolism (first pass effect). Particular examples of active principles are one or more amongst hormones, such as estriol, estradiol, testosterone, progesterone and pregnenolone.

Optionally, the composition of the present invention contains one of more permeation promoters. Without excluding any other, suitable permeation promoters include one or more among dimethyl sulfoxide, diethyleneglycol monoethyl ether, propylene glycol, dicaprylocaprate, isopropyl myristate, sodium laurylsulfate, polyoxyethylene sorbitan and sorbitan monolaurate. Particularly, diethylene glycol monoethyl ether is used.

Also optionally, the composition of the invention contains one or more preservative/conservation agents, to prevent microbial contamination. Without excluding other agent, preferred examples thereof include wide spectrum preservatives such as the ones that act against gram positive and gram negative bacteria, fungi and yeast. Suitable examples include one or more amongst *Lonicera japonica* extract, *Usnea barbata* extract, ferulic acid, anisic acid, tocopherol, glyceryl laurate, hinokitiol (isopropyltropolone). Particularly, *Lonicera japonica* extract is used.

In an additional aspect, the invention is directed to a simple improved process for producing the above mentioned stable topical composition.

Thus, in another aspect the present invention concerns a process for producing a topical composition for dermal or transdermal administration of one or more active principles, involving the preparation of a base nanoemulsion followed by the incorporation of one or more active principles characterized by comprising the following steps:

a. Preparing a first mixture of humectant with a portion of the total water, and heating the mixture.
b. Preparing a second mixture containing emollient and surfactant, until solubilization, adding a non-ionic emulsifying agent, and then heating the mixture.
c. bringing both mixtures (a) in (b) to a temperature between about 70 and 80° C., discontinuing the heating, pouring the mixture of (a) onto the mixture of (b), under constant agitation, until a homogeneous emulsion is obtained;
d. Under agitation, removing the heating until a temperature lower than about 40° C. is reached, and then pouring onto it a pre-prepared solution of hydrating agent with the remaining of the total water; keeping under vigorous agitation, preferably for at least two hours.
e. If the active principle is solid, submitting same to atomization before the following step.
f. Optionally, adding to the active principle one or more of the following: a permeation promoter, an oleous vehicle, an oxidizing agent and a hydrating agent, homogenizing the mixture.
g. Adding the mixture of step (f) to the emulsion of step (d).
h. Grinding the emulsion obtained until completely homogenized.
i. Optionally, mixing the oxygen-carrying agent.
j. If necessary, adjusting the pH of the emulsion to between about 6 and 7.

Steps (a) the (d) are related to the preparation of the base nanoemulsion of the stable topical composition of the invention.

Preferably, the water used here is demineralized water.

Particularly, a preservative is also added to the pre-prepared aqueous solution of hydrating agent used in step (d), the pH of which is neutralized with a suitable acidifying agent, for example, a solution of 5% citric acid. Particularly, after step (d) the emulsion is left to rest for a period of a few hours, particularly between 12 and 24 hours, and then the pH is adjusted between about 7.5 and 7.8.

The oleous vehicle in step (f) is, for example, an odorless oil, particularly olive oil. Preferably, the homogenization in this step is mild.

In a suitable composition of the invention, without excluding any other, adequate amounts of the components are as follows, being understood that variations of about more or less 20% are encompassed by the invention:
non-ionic emulsifying agent—6%
emollient: 5%
surfactant: 3%
humectant: 5%
hydrating agent: 1%
microbicidal preservative/conservation agent: 0.5%
acidifying agent: qs
solubilizing water: qsp The percentages above are of weight of the component in relation to the total weight of the ingredients used in steps (a) to (d) for the preparation of the base nanoemulsion.

As to the other ingredients, the same mentioned variation above also applies:
active principle: typically 1 through 20%
oxygen-carrying agent: 1%
hydrating agent: 1%
permeation promoter: 10%
oleous vehicle: 5%
base nanoemulsion: qsp 100%

The percentages of the latter ingredients are of weight of the ingredient in relation to the total weight of all the ingredients of the composition.

Example of an Embodiment of a Stable Topical Hormone Composition

In a suitable container, a PHASE A was prepared by mixing 75 g of demineralized water and 5 g of propyleneglycol (humectant), and heating the mixture until between 70 and 80° C., under agitation.

In another container, a PHASE B was prepared by adding 7 g of a commercial emollient (a mixture of 35 to 46.3% linolenic acid, 20.5 to 29% acid linoleic acid, 15.4 to 31.6% oleic acid, 2.9 to 6.7% palmitic acid, and about 1% of a mixture of capric and caprylic acids), and 3 g of lecithin (amphoteric surfactant) to solubilize each other, and then 9 g of a commercial emulsifying agent containing cetearyl olivate, sorbitan olivate and ceteareth-6 olivate was added, under agitation and heating up to 70° C.

The aqueous phase A was poured onto the oleous phase B, under constant agitation. The agitation was kept until a smooth homogeneous emulsion was obtained, which was then allowed to cool. Concomitantly, a PHASE C was prepared by solubilizing 1 g of trehalose (hydrating agent) in 1.5 g of demineralized water, and 0.5 g of *Lonicera japonica* extract (preservative), and the pH thereof was neutralized with a sufficient amount of a 50% citric acid solution. When the emulsion (phase A+phase B) cooled down to a temperature below 40° C., phase C was added thereto, and the emulsion was homogenized for further 2 hours, under vigorous agitation. It was left resting for 24 hours after what its pH was adjusted as required.

Up to this point of the process, a base nanoemulsion was prepared, which may be stored for later use.

In a suitable atomizer, two hormones were finely ground, 0.25 g of estriol and 0.1 g of estradiol (active principles).

To this ground matter, in a suitable container, 10 g of diethyleneglycol monoethyl ether (permeation promoter), 5 g of odorless oil (oleous vehicle) were added, and they were homogenized. Afterwards, the solubilized powder was transferred to a container containing 84 g of the base nanoemulsion, and it was homogenized slowly. Finally, 1 g of liposome of perfluorodecaline (oxygen-carrying agent) was added and mixed up.

The invention claimed is:
1. A stable topical composition, comprising:
(a) a nanoemulsion comprising:
a non-ionic emulsifying agent comprising cetearyl olivate, sorbitan olivate and ceteareth olivate;
an amphoteric surfactant comprising lecithin;

an emollient comprising linolenic acid, linoleic acid and oleic acid;
a humectant comprising propylene glycol;
a hydrating agent comprising trehalose, and
(b) an active principle comprising at least one compound selected from the group consisting of estriol, estradiol, testosterone, progesterone and pregnenolone incorporated in the oleous globules of said nanoemulsion.

2. The topical composition according to claim 1 further comprising:
(c) an oxygen-carrying agent;
(d) an oleous vehicle, and
(e) a permeation promoter.

3. The topical composition according to claim 2, wherein said oxygen-carrying agent comprises perfluorodecalin and perfluorotripropylamine.

4. The topical composition according to claim 3 wherein said oxygen-carrying agent is contained in a liposome.

5. The topical composition according to claim 4 wherein said liposome is a phosphatidylcholine liposome.

6. The topical composition according to claim 1 further comprising a permeation promoter selected from a group consisting of: dimethyl sulfoxide, diethylene glycol monoethyl ether, propylene glycol dicaprylocaprate, isopropyl myristate, sorbitan sodium lauryl sulfate, polyoxyethylene monooleate, and sorbitan monolaurate.

7. The topical composition according to claim 1 further comprising a preservative agent.

8. The topical composition according to claim 7, wherein said preservative agent is selected from a group consisting of: an extract of *Lonicera japonica*, an extract of *Usnea barbata*, ferulic acid, anisic acid, tocopherol, glyceryl laurate, and isopropyltropolone.

* * * * *